(12) United States Patent
Moffitt et al.

(10) Patent No.: US 8,929,990 B2
(45) Date of Patent: *Jan. 6, 2015

(54) TRANSVASCULAR NEURAL STIMULATION DEVICE AND METHOD FOR TREATING HYPERTENSION

(75) Inventors: Julia Moffitt, Iowa City, IA (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1046 days.

This patent is subject to a terminal disclaimer.

(21) Appl. No.: 12/968,831

(22) Filed: Dec. 15, 2010

(65) Prior Publication Data

US 2011/0082537 A1     Apr. 7, 2011

Related U.S. Application Data

(63) Continuation of application No. 12/371,153, filed on Feb. 13, 2009, now abandoned, which is a continuation of application No. 11/103,245, filed on Apr. 11, 2005, now Pat. No. 7,499,748.

(51) Int. Cl.
  *A61N 1/36* (2006.01)
  *A61N 1/05* (2006.01)
  *A61N 1/362* (2006.01)

(52) U.S. Cl.
  CPC .............. *A61N 1/056* (2013.01); *A61N 1/3627* (2013.01); *A61N 1/36114* (2013.01)
  USPC ......................................................... 607/44

(58) Field of Classification Search
  None
  See application file for complete search history.

(56) References Cited

U.S. PATENT DOCUMENTS

| | | | |
|---|---|---|---|
| 3,650,277 | A | 3/1972 | Sjostrand et al. |
| 3,692,027 | A | 9/1972 | Ellinwood, Jr. |
| 4,003,379 | A | 1/1977 | Ellinwood, Jr. |

(Continued)

FOREIGN PATENT DOCUMENTS

| | | |
|---|---|---|
| EP | 0467695 A2 | 1/1992 |
| EP | 0547734 A2 | 6/1993 |

(Continued)

OTHER PUBLICATIONS

"U.S. Appl. No. 11/103,245, Non-Final Office Action mailed Jan. 11, 2008", 9 pgs.

(Continued)

*Primary Examiner* — Kennedy Schaetzle
(74) *Attorney, Agent, or Firm* — Schwegman Lundberg & Woessner, P.A.

(57) ABSTRACT

This document discusses, among other things, apparatus, systems, and methods for transvascularly stimulation of a nerve or nerve trunk. In an example, an apparatus is configured to transvascularly stimulate a nerve trunk through a blood vessel. The apparatus includes an expandable electrode that is chronically implantable in a blood vessel proximate a nerve trunk. The expandable electrode is configured to abut a predetermined surface area of the vessel wall along a predetermined length of the vessel. An electrical lead is coupled to the expandable electrode. An implantable pulse generator is coupled to the lead and configured to deliver an electrical stimulation signal to the electrode through the lead. In an example method, an electrical signal is delivered from an implanted medical device to an electrode chronically implanted in a blood vessel proximate a nerve trunk to transvascularly deliver neural stimulation from the electrode to the nerve trunk.

28 Claims, 12 Drawing Sheets

(56) References Cited

U.S. PATENT DOCUMENTS

| | | |
|---|---|---|
| 4,082,097 A | 4/1978 | Mann et al. |
| 4,146,029 A | 3/1979 | Ellinwood, Jr. |
| 4,217,910 A | 8/1980 | Khalil |
| 4,522,208 A | 6/1985 | Buffet |
| 4,871,351 A | 10/1989 | Feingold |
| 4,944,299 A | 7/1990 | Silvian |
| 4,987,897 A | 1/1991 | Funke |
| 5,042,497 A | 8/1991 | Shapland |
| 5,052,388 A | 10/1991 | Sivula et al. |
| 5,111,815 A | 5/1992 | Mower |
| 5,199,428 A | 4/1993 | Obel et al. |
| 5,203,326 A | 4/1993 | Collins |
| 5,300,875 A | 4/1994 | Tuttle |
| 5,318,592 A | 6/1994 | Schaldach |
| 5,324,316 A | 6/1994 | Schulman et al. |
| 5,330,507 A | 7/1994 | Schwartz |
| 5,342,408 A | 8/1994 | deCoriolis et al. |
| 5,354,318 A | 10/1994 | Taepke |
| 5,436,548 A | 7/1995 | Thomas |
| 5,496,360 A | 3/1996 | Hoffmann et al. |
| 5,501,703 A | 3/1996 | Holsheimer et al. |
| 5,522,854 A | 6/1996 | Ideker et al. |
| 5,531,779 A | 7/1996 | Dahl et al. |
| 5,540,730 A | 7/1996 | Terry, Jr. et al. |
| 5,551,953 A | 9/1996 | Lattin et al. |
| 5,562,711 A | 10/1996 | Yerich et al. |
| 5,562,713 A | 10/1996 | Silvian |
| 5,578,061 A | 11/1996 | Stroetmann et al. |
| 5,651,378 A | 7/1997 | Matheny et al. |
| 5,658,318 A | 8/1997 | Stroetmann et al. |
| 5,662,689 A | 9/1997 | Elsberry et al. |
| 5,700,282 A | 12/1997 | Zabara |
| 5,707,400 A | 1/1998 | Terry, Jr. et al. |
| 5,730,125 A | 3/1998 | Prutchi et al. |
| 5,775,338 A | 7/1998 | Hastings |
| 5,792,187 A | 8/1998 | Adams |
| 5,800,498 A | 9/1998 | Obino et al. |
| 5,814,089 A | 9/1998 | Stokes et al. |
| 5,817,131 A | 10/1998 | Elsberry et al. |
| 5,843,142 A | 12/1998 | Sultan |
| 5,846,218 A | 12/1998 | Brisken et al. |
| 5,913,876 A | 6/1999 | Taylor et al. |
| 5,916,239 A | 6/1999 | Geddes et al. |
| 5,972,029 A | 10/1999 | Fuisz |
| 6,006,134 A | 12/1999 | Hill et al. |
| 6,073,048 A | 6/2000 | Kieval et al. |
| 6,115,636 A | 9/2000 | Ryan |
| 6,117,085 A | 9/2000 | Picatti et al. |
| 6,134,470 A | 10/2000 | Hartlaub |
| 6,140,740 A | 10/2000 | Porat et al. |
| 6,141,588 A | 10/2000 | Cox et al. |
| 6,164,284 A | 12/2000 | Schulman et al. |
| 6,179,824 B1 | 1/2001 | Eggers et al. |
| 6,205,361 B1 | 3/2001 | Kuzma et al. |
| 6,206,914 B1 | 3/2001 | Soykan et al. |
| 6,213,942 B1 | 4/2001 | Flach et al. |
| 6,231,516 B1 | 5/2001 | Keilman et al. |
| 6,237,398 B1 | 5/2001 | Porat et al. |
| 6,240,316 B1 | 5/2001 | Richmond et al. |
| 6,266,564 B1 | 7/2001 | Hill et al. |
| 6,278,894 B1 | 8/2001 | Salo et al. |
| 6,292,695 B1 | 9/2001 | Webster, Jr. et al. |
| 6,292,703 B1 | 9/2001 | Meier et al. |
| 6,308,104 B1 | 10/2001 | Taylor et al. |
| 6,317,615 B1 | 11/2001 | KenKnight et al. |
| 6,341,236 B1 | 1/2002 | Osorio et al. |
| 6,349,233 B1 | 2/2002 | Adams |
| 6,358,202 B1 | 3/2002 | Arent |
| 6,375,666 B1 | 4/2002 | Mische |
| 6,381,499 B1 | 4/2002 | Taylor et al. |
| 6,400,982 B2 | 6/2002 | Sweeney et al. |
| 6,445,953 B1 | 9/2002 | Bulkes et al. |
| 6,449,507 B1 | 9/2002 | Hill et al. |
| 6,453,195 B1 | 9/2002 | Thompson |
| 6,456,866 B1 | 9/2002 | Tyler et al. |
| 6,473,644 B1 | 10/2002 | Terry, Jr. et al. |
| 6,477,418 B2 | 11/2002 | Plicchi et al. |
| 6,511,500 B1 | 1/2003 | Rahme |
| 6,518,245 B1 | 2/2003 | Anderson et al. |
| 6,519,488 B2 | 2/2003 | KenKnight et al. |
| 6,522,926 B1 | 2/2003 | Kieval et al. |
| 6,532,388 B1 | 3/2003 | Hill et al. |
| 6,542,774 B2 | 4/2003 | Hill et al. |
| 6,564,096 B2 | 5/2003 | Mest |
| 6,584,362 B1 | 6/2003 | Scheiner et al. |
| 6,609,023 B1 | 8/2003 | Fischell et al. |
| 6,622,041 B2 | 9/2003 | Terry, Jr. et al. |
| 6,628,987 B1 | 9/2003 | Hill et al. |
| 6,645,145 B1 | 11/2003 | Dreschel et al. |
| 6,656,960 B2 | 12/2003 | Puskas |
| 6,668,191 B1 | 12/2003 | Boveja |
| 6,690,971 B2 | 2/2004 | Schauerte et al. |
| 6,735,471 B2 | 5/2004 | Hill et al. |
| 6,764,498 B2 | 7/2004 | Mische |
| 6,778,854 B2 | 8/2004 | Puskas |
| 6,788,970 B1 | 9/2004 | Park et al. |
| 6,798,716 B1 | 9/2004 | Charych |
| 6,802,811 B1 | 10/2004 | Slepian |
| 6,804,561 B2 | 10/2004 | Stover |
| 6,805,998 B2 | 10/2004 | Jenson et al. |
| RE38,705 E | 2/2005 | Hill et al. |
| 6,904,318 B2 | 6/2005 | Hill et al. |
| 6,912,419 B2 | 6/2005 | Hill et al. |
| 6,934,583 B2 | 8/2005 | Weinberg et al. |
| 6,937,896 B1 | 8/2005 | Kroll |
| 7,010,345 B2 | 3/2006 | Hill et al. |
| 7,123,959 B2 | 10/2006 | Cates |
| 7,194,313 B2 | 3/2007 | Libbus |
| 7,218,964 B2 | 5/2007 | Hill et al. |
| 7,236,821 B2 | 6/2007 | Cates et al. |
| 7,245,967 B1 | 7/2007 | Shelchuk |
| 7,260,431 B2 | 8/2007 | Libbus et al. |
| 7,277,761 B2 | 10/2007 | Shelchuk |
| 7,294,334 B1 | 11/2007 | Michal et al. |
| 7,300,449 B2 | 11/2007 | Mische |
| 7,305,265 B2 | 12/2007 | Fukui |
| 7,321,793 B2 | 1/2008 | Ben Ezra et al. |
| 7,403,819 B1 | 7/2008 | Shelchuk et al. |
| 7,460,906 B2 | 12/2008 | Libbus |
| 7,486,991 B2 | 2/2009 | Libbus et al. |
| 7,493,161 B2 | 2/2009 | Libbus et al. |
| 7,499,748 B2 | 3/2009 | Moffitt et al. |
| 7,509,166 B2 | 3/2009 | Libbus |
| 7,542,800 B2 | 6/2009 | Libbus et al. |
| 7,548,780 B2 | 6/2009 | Libbus et al. |
| 7,551,958 B2 | 6/2009 | Libbus et al. |
| 7,555,341 B2 | 6/2009 | Moffitt et al. |
| 7,561,923 B2 | 7/2009 | Libbus et al. |
| 7,570,999 B2 | 8/2009 | Libbus et al. |
| 7,587,238 B2 | 9/2009 | Moffitt et al. |
| 7,616,990 B2 | 11/2009 | Chavan et al. |
| 7,616,997 B2 | 11/2009 | Kieval et al. |
| 7,617,003 B2 | 11/2009 | Caparso et al. |
| 7,647,114 B2 | 1/2010 | Libbus |
| 7,657,312 B2 | 2/2010 | Pastore et al. |
| 7,660,628 B2 | 2/2010 | Libbus et al. |
| 7,706,884 B2 | 4/2010 | Libbus |
| 7,711,421 B2 | 5/2010 | Shafer et al. |
| 7,769,450 B2 | 8/2010 | Libbus et al. |
| 7,783,353 B2 | 8/2010 | Libbus et al. |
| 7,840,266 B2 | 11/2010 | Libbus |
| 7,840,278 B1 | 11/2010 | Puskas |
| 7,949,400 B2 * | 5/2011 | Kieval et al. ............ 607/44 |
| 8,126,561 B2 | 2/2012 | Chavan et al. |
| 8,175,705 B2 * | 5/2012 | Libbus ............ 607/14 |
| 8,634,921 B2 | 1/2014 | Chavan et al. |
| 8,660,648 B2 | 2/2014 | Chavan et al. |
| 2002/0004670 A1 | 1/2002 | Florio et al. |
| 2002/0026221 A1 | 2/2002 | Hill et al. |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0042637 A1 | 4/2002 | Stover |
| 2002/0072776 A1 | 6/2002 | Osorio et al. |

(56) References Cited

U.S. PATENT DOCUMENTS

| | | |
|---|---|---|
| 2002/0107553 A1 | 8/2002 | Hill et al. |
| 2002/0107557 A1 | 8/2002 | Edell et al. |
| 2002/0116030 A1 | 8/2002 | Rezai |
| 2002/0120304 A1 | 8/2002 | Mest |
| 2002/0138123 A1* | 9/2002 | Casas-Bejar et al. ......... 607/120 |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2002/0183237 A1 | 12/2002 | Puskas |
| 2002/0183793 A1 | 12/2002 | Struble et al. |
| 2002/0198570 A1 | 12/2002 | Puskas |
| 2002/0198571 A1 | 12/2002 | Puskas |
| 2003/0004549 A1 | 1/2003 | Hill et al. |
| 2003/0023279 A1 | 1/2003 | Spinelli et al. |
| 2003/0040774 A1 | 2/2003 | Terry, Jr. et al. |
| 2003/0045909 A1 | 3/2003 | Gross et al. |
| 2003/0045914 A1 | 3/2003 | Cohen et al. |
| 2003/0060848 A1 | 3/2003 | Keival et al. |
| 2003/0060857 A1 | 3/2003 | Perrson et al. |
| 2003/0060858 A1 | 3/2003 | Kieval et al. |
| 2003/0069606 A1 | 4/2003 | Girouard et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0114905 A1 | 6/2003 | Kuzma |
| 2003/0132731 A1 | 7/2003 | Chung |
| 2003/0158584 A1 | 8/2003 | Cates et al. |
| 2003/0181951 A1 | 9/2003 | Cates |
| 2003/0195578 A1 | 10/2003 | Perron et al. |
| 2003/0199958 A1 | 10/2003 | Zhang et al. |
| 2003/0212440 A1 | 11/2003 | Boveja |
| 2003/0212445 A1 | 11/2003 | Weinberg |
| 2003/0229380 A1 | 12/2003 | Adams et al. |
| 2004/0010303 A1 | 1/2004 | Bolea et al. |
| 2004/0019364 A1 | 1/2004 | Kieval et al. |
| 2004/0030362 A1 | 2/2004 | Hill et al. |
| 2004/0049235 A1 | 3/2004 | Deno et al. |
| 2004/0059383 A1 | 3/2004 | Puskas |
| 2004/0111118 A1 | 6/2004 | Hill et al. |
| 2004/0122477 A1 | 6/2004 | Whitehurst et al. |
| 2004/0138721 A1 | 7/2004 | Osorio et al. |
| 2004/0172074 A1 | 9/2004 | Yoshihito |
| 2004/0172075 A1 | 9/2004 | Shafer et al. |
| 2004/0186517 A1 | 9/2004 | Hill et al. |
| 2004/0186531 A1 | 9/2004 | Jahns et al. |
| 2004/0193231 A1 | 9/2004 | David et al. |
| 2004/0199210 A1 | 10/2004 | Shelchuk |
| 2004/0215289 A1 | 10/2004 | Fukui |
| 2004/0220621 A1 | 11/2004 | Zhou et al. |
| 2004/0254616 A1 | 12/2004 | Rossing et al. |
| 2005/0018784 A1 | 1/2005 | Kurobe et al. |
| 2005/0021092 A1 | 1/2005 | Yun et al. |
| 2005/0065553 A1 | 3/2005 | Ben Ezra et al. |
| 2005/0065575 A1 | 3/2005 | Dobak |
| 2005/0085864 A1 | 4/2005 | Schulman et al. |
| 2005/0096705 A1 | 5/2005 | Pastore et al. |
| 2005/0096707 A1 | 5/2005 | Hill et al. |
| 2005/0131467 A1 | 6/2005 | Boveja |
| 2005/0143412 A1 | 6/2005 | Puskas |
| 2005/0143779 A1 | 6/2005 | Libbus |
| 2005/0143785 A1 | 6/2005 | Libbus |
| 2005/0143787 A1 | 6/2005 | Boveja et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0187584 A1 | 8/2005 | Denker et al. |
| 2005/0187586 A1 | 8/2005 | David et al. |
| 2005/0197600 A1 | 9/2005 | Schuler et al. |
| 2005/0197675 A1 | 9/2005 | David et al. |
| 2005/0251216 A1 | 11/2005 | Hill et al. |
| 2005/0261741 A1 | 11/2005 | Libbus et al. |
| 2006/0079945 A1 | 4/2006 | Libbus |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0217772 A1 | 9/2006 | Libbus et al. |
| 2006/0229677 A1 | 10/2006 | Moffitt et al. |
| 2006/0259107 A1 | 11/2006 | Caparso et al. |
| 2006/0271115 A1 | 11/2006 | Ben-Ezra et al. |
| 2006/0271118 A1 | 11/2006 | Libbus et al. |
| 2006/0282131 A1 | 12/2006 | Caparso et al. |
| 2007/0021797 A1 | 1/2007 | Kieval et al. |
| 2007/0038259 A1 | 2/2007 | Kieval et al. |
| 2007/0038262 A1 | 2/2007 | Kieval et al. |
| 2007/0093875 A1 | 4/2007 | Chavan et al. |
| 2007/0191904 A1 | 8/2007 | Libbus et al. |
| 2007/0276453 A1 | 11/2007 | Hill et al. |
| 2008/0021507 A1 | 1/2008 | Libbus et al. |
| 2008/0125843 A1 | 5/2008 | Ben-David et al. |
| 2008/0228238 A1 | 9/2008 | Libbus |
| 2009/0048641 A1 | 2/2009 | Libbus |
| 2009/0143834 A1 | 6/2009 | Libbus |
| 2009/0143838 A1 | 6/2009 | Libbus et al. |
| 2009/0149900 A1 | 6/2009 | Moffitt et al. |
| 2010/0049275 A1 | 2/2010 | Chavan et al. |
| 2010/0228308 A1 | 9/2010 | Cowan et al. |
| 2012/0158090 A1 | 6/2012 | Chavan et al. |
| 2013/0073000 A1 | 3/2013 | Chavan et al. |

FOREIGN PATENT DOCUMENTS

| | | |
|---|---|---|
| EP | 1304135 A2 | 4/2003 |
| EP | 1486232 A2 | 12/2004 |
| EP | 1541193 A1 | 6/2005 |
| JP | 2004173791 A | 6/2004 |
| NO | WO-2004084993 A1 | 10/2004 |
| WO | WO-9216257 A1 | 10/1992 |
| WO | WO-94/07564 A2 | 4/1994 |
| WO | WO-96/39932 A1 | 12/1996 |
| WO | WO-9713550 A1 | 4/1997 |
| WO | WO-97/33513 A1 | 9/1997 |
| WO | WO-9740885 A1 | 11/1997 |
| WO | WO-99/65561 A1 | 12/1999 |
| WO | WO-0226318 A1 | 4/2002 |
| WO | WO-0226320 A1 | 4/2002 |
| WO | WO-0234327 A2 | 5/2002 |
| WO | WO-02085448 A2 | 10/2002 |
| WO | WO-02096512 A1 | 12/2002 |
| WO | WO-03/076008 A1 | 9/2003 |
| WO | WO-03/082080 A2 | 10/2003 |
| WO | WO-03/105658 A2 | 12/2003 |
| WO | WO-03099377 A1 | 12/2003 |
| WO | WO-2004012814 A1 | 2/2004 |
| WO | WO-2004084990 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2004110550 A2 | 12/2004 |
| WO | WO-2005018739 A1 | 3/2005 |
| WO | WO-2005/042091 A1 | 5/2005 |
| WO | WO-2005053788 A1 | 6/2005 |
| WO | WO-2005/063332 A1 | 7/2005 |
| WO | WO-2005/065771 A1 | 7/2005 |
| WO | WO-2005113066 A1 | 12/2005 |
| WO | WO-2006031331 A1 | 3/2006 |
| WO | WO-2006/069215 A2 | 6/2006 |
| WO | WO-2006/110338 A1 | 10/2006 |
| WO | WO-2007/050657 A1 | 5/2007 |
| WO | WO-2008063396 A1 | 5/2008 |

OTHER PUBLICATIONS

"U.S. Appl. No. 11/103,245, Notice of Allowance mailed Oct. 20, 2008", 4 pgs.

(56) References Cited

OTHER PUBLICATIONS

"U.S. Appl. No. 11/103,245, Response filed Jul. 11, 2008 to Non-Final Office Action mailed Jan. 11, 2008", 14 pgs.

"U.S. Appl. No. 11/103,245, Response filed Oct. 17, 2007 to Restriction Requirement mailed Sep. 18, 2007", 7 pgs.

"U.S. Appl. No. 11/103,245, Restriction Requirement mailed Sep. 18, 2007", 6 pgs.

"U.S. Appl. No. 11/130,022, Non-Final Office Action mailed Jan. 28, 2009", 6 pgs.

"U.S. Appl. No. 11/130,022, Non-Final Office Action mailed May 15, 2008", 9 pgs.

"U.S. Appl. No. 11/130,022, Notice of Allowance mailed Jul. 21, 2009", 6 pgs.

"U.S. Appl. No. 11/130,022, Response filed Apr. 28, 2009 to Non Final Office Action mailed Jan. 28, 2009", 11 pgs.

"U.S. Appl. No. 11/130,022, Response filed Aug. 15, 2008 to Non-Final Office Action mailed May 15, 2008", 18 pgs.

"U.S. Appl. No. 11/256,907, Final Office Action mailed Mar. 27, 2009", 8 pgs.

"U.S. Appl. No. 11/256,907, Non-Final Office Action mailed Jul. 8, 2008", 6 pgs.

"U.S. Appl. No. 11/256,907, Notice of Allowance mailed Jul. 1, 2009", 5 pgs.

"U.S. Appl. No. 11/256,907, Response and Preliminary Amendment filed Apr. 21, 2008 to Restriction Requirement mailed Mar. 21, 2008", 9 pgs.

"U.S. Appl. No. 11/256,907, Response filed May 27, 2009 to Final Office Action mailed Mar. 27, 2009", 10 pgs.

"U.S. Appl. No. 11/256,907, Response filed Nov. 7, 2008 to Non-Final Office Action mailed Jul. 8, 2008", 12 pgs.

"U.S. Appl. No. 11/256,907, Restriction Requirement mailed Mar. 21, 2008", 11 pgs.

"European Application Serial No. 06836504.8, Communication mailed Jun. 2, 2008", 2 pgs.

"European Application Serial No. 06836504.8, Communication mailed Oct. 9, 2008", 5 pgs.

"European Application Serial No. 06836504.8, Decision to Refuse a European Patent Application mailed Jun. 22, 2010", 31 pgs.

"European Application Serial No. 06836504.8, Grounds of Appeal Filed/ Written Statements Filed Oct. 25, 2010", 40 pgs.

"European Application Serial No. 06836504.8, Response filed Feb. 19, 2009 to Communication mailed Oct. 9, 2008", 7 pgs.

"European Application Serial No. 06836504.8, Summons to Attend Oral Proceedings mailed Mar. 9, 2010", 11 pgs.

"European Application Serial No. 06836504.8, Summons to Attend Oral Proceedings mailed Nov. 13, 2009", 6 pgs.

"International Application Serial No. PCT/US2006/011882, International Search Report and Written Opinion mailed Aug. 2, 2006", 13 pgs.

"International Application Serial No. PCT/US2006/041569", International Search Report and Written Opinion mailed Mar. 7, 2007, 14 pgs.

"Structural Remodeling of Cardiac Myocytes in Hypertrophy and Progression to Failure; and, on Atrial Remodeling and Drug Treatment of Atrial Fibrillation", *In Cardia Remodeling And Failure, in Section II, Remodeling and Heart Failure*, Singal, et al., editors; Kluwer Academic Publishers, (2003), 183-93; 319-330.

Caparso, A., "System for Selective Activation of a Nerve Trunk Using a Transvascular Reshaping Lead", U.S. Appl. No. 11/130,022, filed May 16, 2005, 33 Pgs.

Carr, W. N., "Integrated Pressure Sensor With Remote Power Source and Remote Readout", The 8th International Conference on Solid-State Sensors and Actuators and Eurosensors IX, *Digest of Technical Papers*, Stockholm, Sweden, (Jun. 25-29, 1995), 624-627.

Dunlap, M. E., et al., "Mechanisms of altered vagal control in heart failure: influence of muscarinic receptors and acetylcholinesterase activity", *Am J Physiol Heart Circ Physiol.*, 285(4), (Oct. 2003), H1632-40.

Grassi, G., et al., "Sympathetic response to ventricular extrasystolic beats in hypertension and heart failure", *Hypertension*, 39(4), (Apr. 2002), 886-91.

Jacobsson, F., et al., "The effect of transcutaneous electric nerve stimulation in patients with therapy-resistant hypertension", *J Hum Hypertens.*, 14(12), (Dec. 2000), 795-8.

Janes, R. D., et al., "Anatomy of human extrinsic cardiac nerves and ganglia.", *Am J Cardiol.*, 57(4), (Feb. 1, 1986), 299-309.

Leventhal, D K, et al., "Subfascicle stimulation selectivity with the flat interface nerve electrode", *Annals of Biomedical Engineering*, 31(6), (Jun. 2003), 643-52.

Li, M., et al., "Vagal nerve stimulation markedly improves long-term survival after chronic heart failure in rats", *Circulation*, 109(1), (2004), 120-124.

Nolan, J., et al., "Prospective Study of Heart Rate Variability and Mortality in Chronic Heart Failure: Results of the United Kingdom Heart Failure Evaluation and Assessment of Risk Trial (UK-Heart)", *Circulation*, 98(15), (1998), 1510-1516.

Schauerte, P, et al., "Catheter stimulation of cardiac parasympathetic nerves in humans: a novel approach to the cardiac autonomic nervous system". *Circulation*, 104(20), (Nov. 13, 2001), 2430-2435.

Schauerte, P. et al., "Ventricular rate control during atrial fibrillation by cardiac parasympathetic nerve stimulation: a transvenous approach", *J Am Coll Cardiol.*, 34(7), (Dec. 1999), 2043-50.

Schauerte, P. N. et al., "Transvenous parasympathetic cardiac nerve stimulation: an approach for stable sinus rate control",*Journal of Cardiovascular Electrophysiology*, 10(11), (Nov. 1999), 1517-1524.

Schauerte, P., et al.,"Transvenous Parasympathetic Nerve Stimulation in the Inferior Vena Cava and Atrioventricular Conduction", *Journal of Cardiovascular Electrophysiology*, 11(1), (Jan. 2000), 64-69.

Scherlag, B. J, et al., "Endovascular stimulation within the left pulmonary artery to induce slowing of heart rate and paroxysmal atrial fibrillation.", *Cardiovasc Research*, 54(2), (May 2002), 470-475.

Scherlag, M A., et al., "Endovascular Neural Stimulation Via a Novel Basket Electrode Catheter: Comparison of Electrode Configurations", *Journal of Interventional Cardiac Electrophysiology*, 4(1), (Apr. 2000), 219-224.

Sigurdsson, A., et al., "The Role of Neurohormonal Activation in Chronic Heart Failure and Postmyocardial Infarction", *American Heart Journal*, 132(1, Part 2), (Jul. 1996), 229-234.

Thompson, G. W, "Bradycardia induced by intravascular versus direct stimulation of the vagus nerve", *Annals of Thoracic Surgery*, 65(3), (Mar. 1998), 637-642.

Tyler, D J, et al., "Chronic response of the rat sciatic nerve to the flat interface nerve electrode", *Annals of Biomedical Engineering*, 31(6), (Jun. 2003), 633-642.

Vanoli, E., et al., "Vagal Stimulation and Prevention of Sudden Death in Conscious Dogs With a Healed Myocardial Infarction", Circulation Research, 68(5), (May 1991), 1471-1481.

Ziaie, B., "A Single-Channel Implantable Microstimulator for Functional Neuromuscular Stimulation", *IEEE Transactions on Biomedical Engineering*, 44, (Oct. 1997), 909-920.

US 8,315,702, 11/2012, Chavan et al. (withdrawn).

\* cited by examiner

TRANSVASCULAR NEURAL STIMULATION DEVICE AND METHOD FOR TREATING HYPERTENSION

CROSS REFERENCE TO RELATED APPLICATION

This application is a continuation of U.S. application Ser. No. 12/371,153, filed Feb. 13, 2009, abandoned, which is a continuation of U.S. application Ser. No. 11/103,245, filed Apr. 11, 2005, now issued at U.S. Pat. No. 7,499,748, which are hereby incorporated by reference in their entirety.

TECHNICAL FIELD

This patent document pertains generally to neural stimulation devices and methods, and more particularly, but not by way of limitation, to transvascular neural stimulation devices and methods.

BACKGROUND

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Some target areas can be difficult to stimulate or isolate. For example, it may be difficult to stimulate a nerve that is located deep in the body or behind an organ. Improved neural stimulation devices are needed.

SUMMARY

Various aspects of the present subject matter relate to an implantable apparatus. In an example, an apparatus is configured to transvascularly stimulate a nerve trunk through a blood vessel. The apparatus includes an expandable electrode that is chronically implantable in a blood vessel proximate a nerve trunk. The expandable electrode is configured to abut an area of the vessel wall along a length of the vessel. An electrical lead is coupled to the expandable electrode. An implantable pulse generator is coupled to the lead and configured to deliver an electrical stimulation signal to the electrode through the lead.

Various aspects of the present subject matter relate to a method. In an example method, an electrical signal is delivered from an implanted medical device to an electrode chronically implanted in a blood vessel proximate a nerve trunk to transvascularly deliver neural stimulation from the electrode to the nerve trunk.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. Additionally, the identified embodiments are not necessarily exclusive of each other, as some embodiments may be able to be combined with other embodiments. The following detailed description is, therefore, not to be taken in a limiting sense, and the scope is defined only by the appended claims, along with the full scope of legal equivalents to which such claims are entitled.

Overview

Figure 1A:
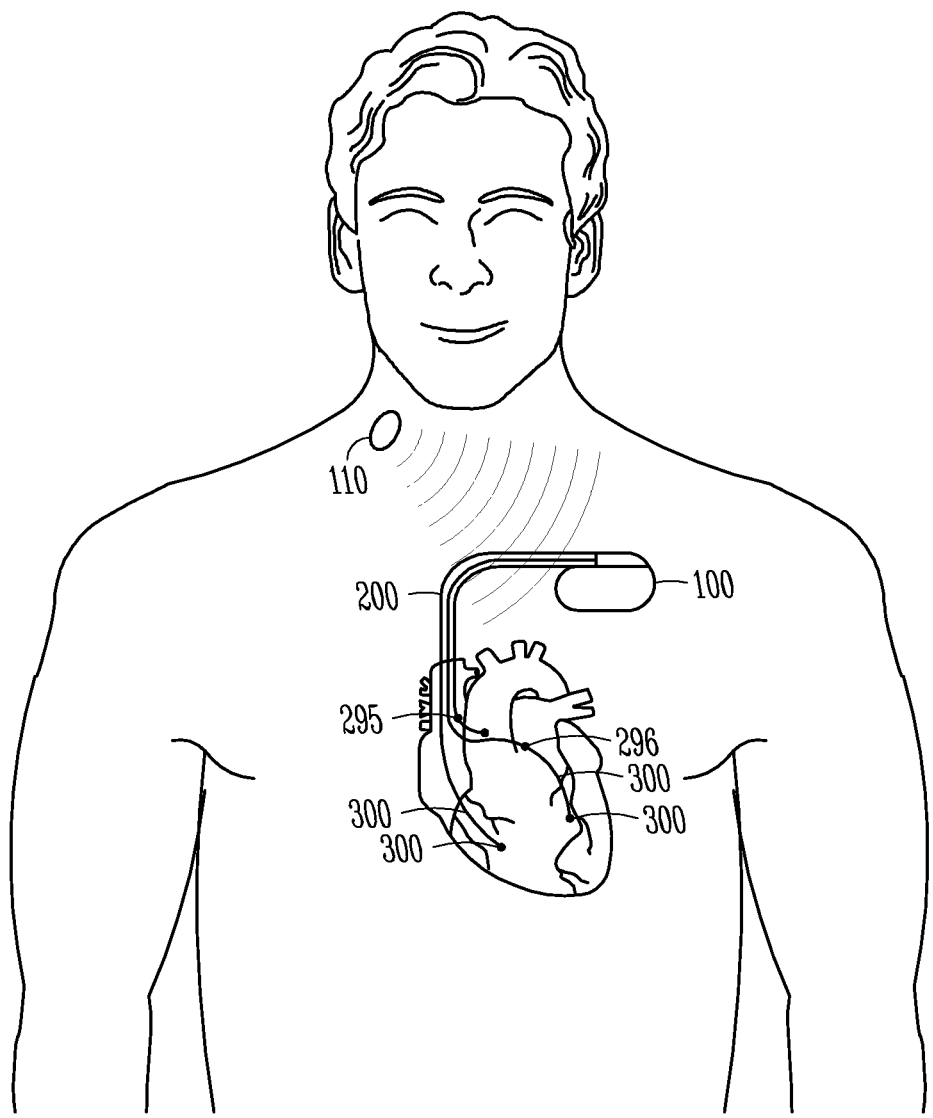
FIG. 1A shows a medical device implanted in a patient and leads extending into a heart, according to embodiments of the present subject matter.

Referring now to FIG. 1A, an embodiment of an implantable cardiac device 100 is placed subcutaneously or submuscularly in a patient's chest with leads 200 extending toward the heart. At least one lead 200 is coupled to an electrode 295 that is placed in a blood vessel and positioned to transvascularly stimulate a nerve on or near the extravascular surface of the vessel. Transvascular stimulation avoids direct contact with nerves during stimulation and reduces problems associated with neural inflammation or injury induced by direct stimulation. Leads can be implanted through the vasculature, thus maintaining the integrity of the thorax. Transvascular stimulation using intravascularly-fed leads provides relatively non-invasive access to anatomical targets and points of innervation in comparison to cuff electrodes.

Figure 1B:
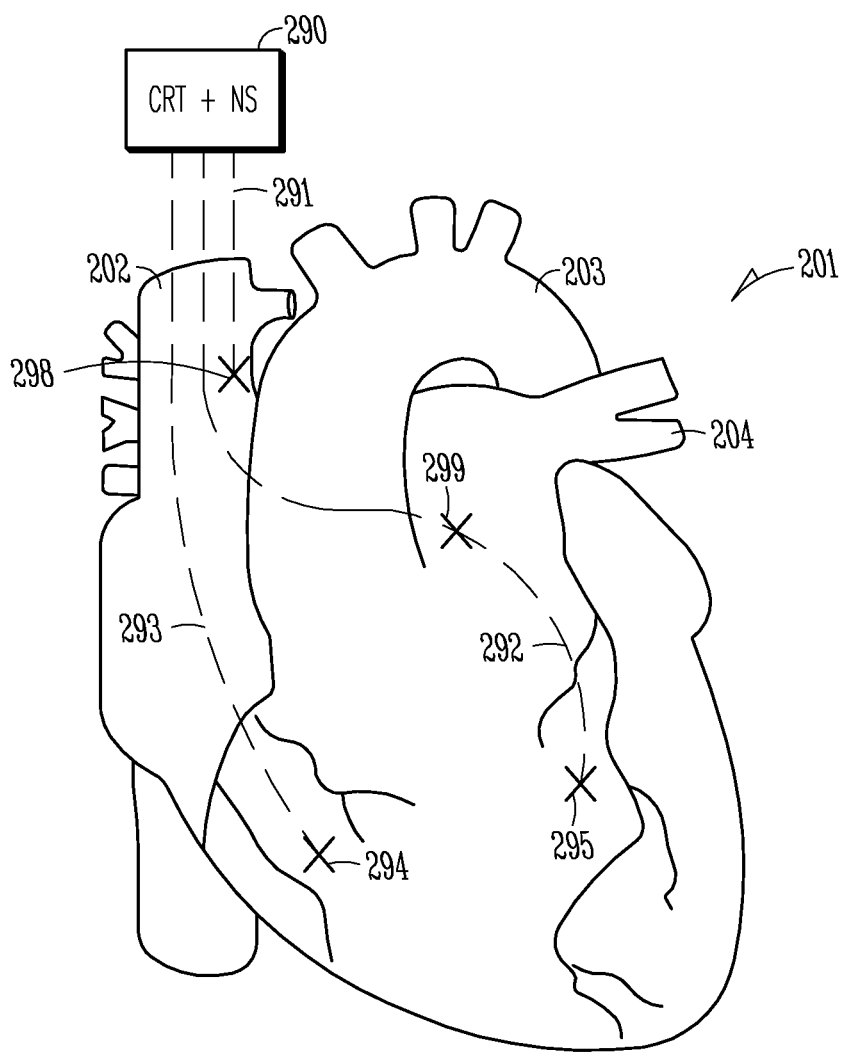
FIG. 1B is an illustration of a heart and leads extending into the heart, according to embodiments of the present subject matter.
Figure 1C:
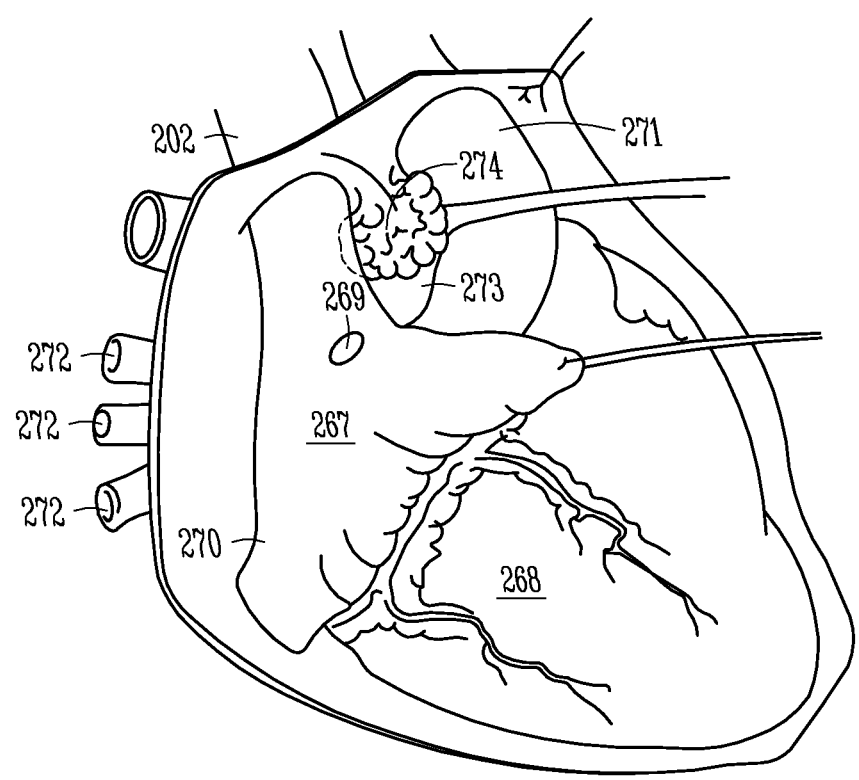
FIGS. 1C and 1D are illustrations of a heart and related blood vessels.
Figure 1D:
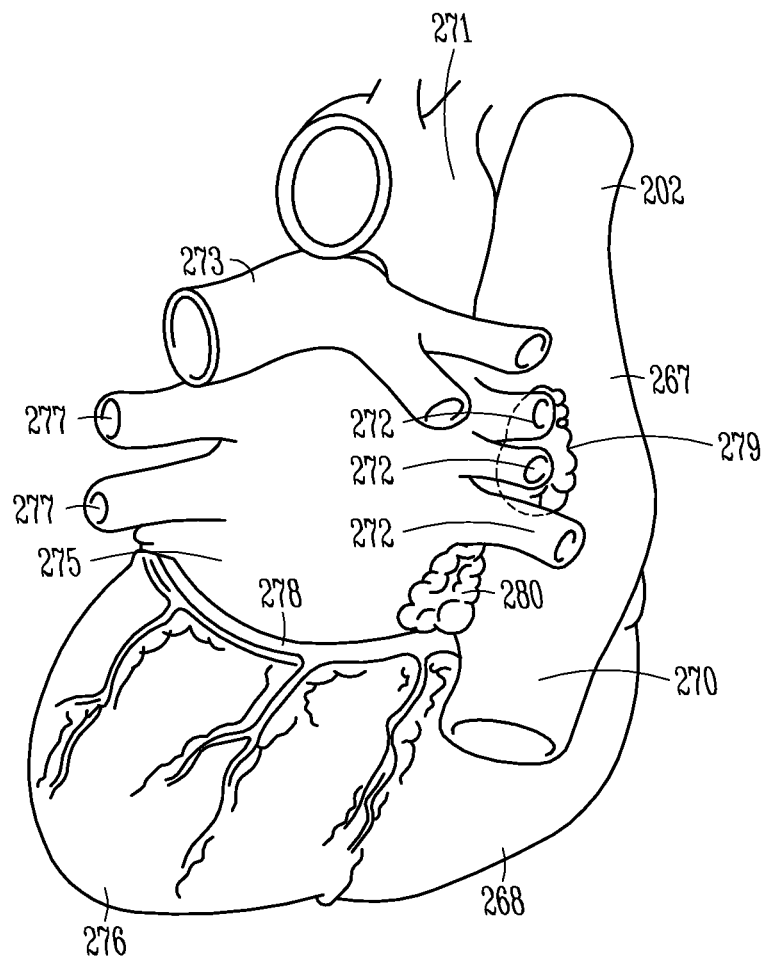
Figure 1E:
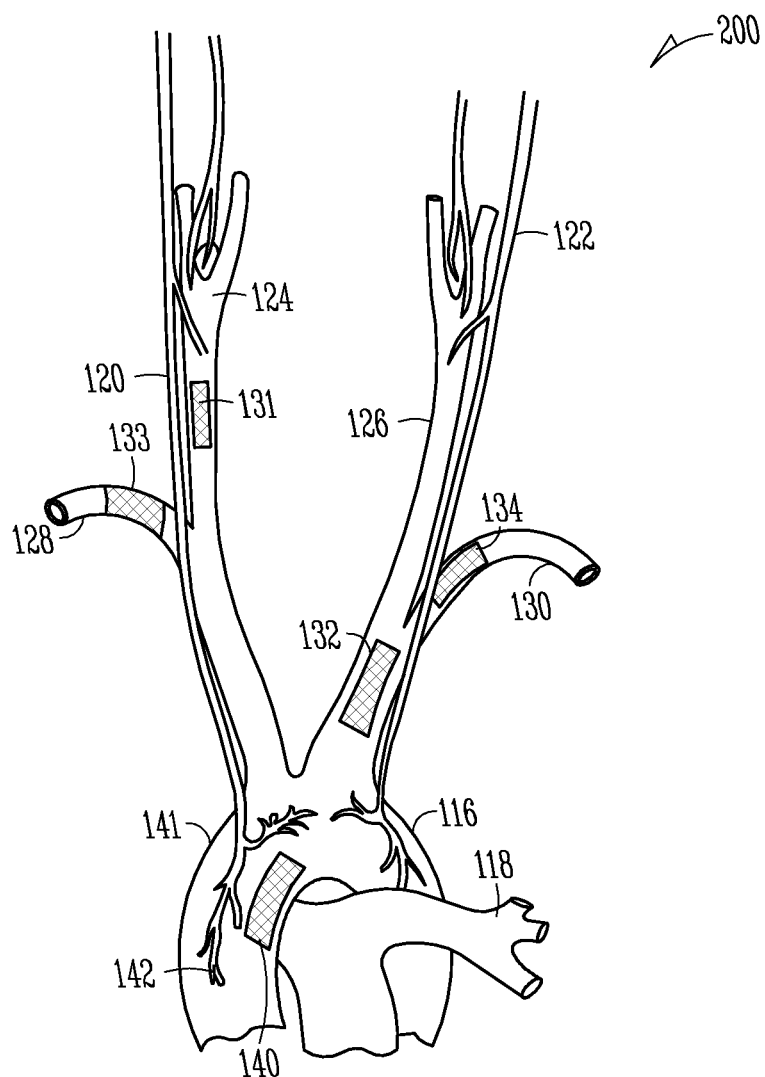
FIG. 1E is an illustration of blood vessels and nerve trunks.
Figure 2A:
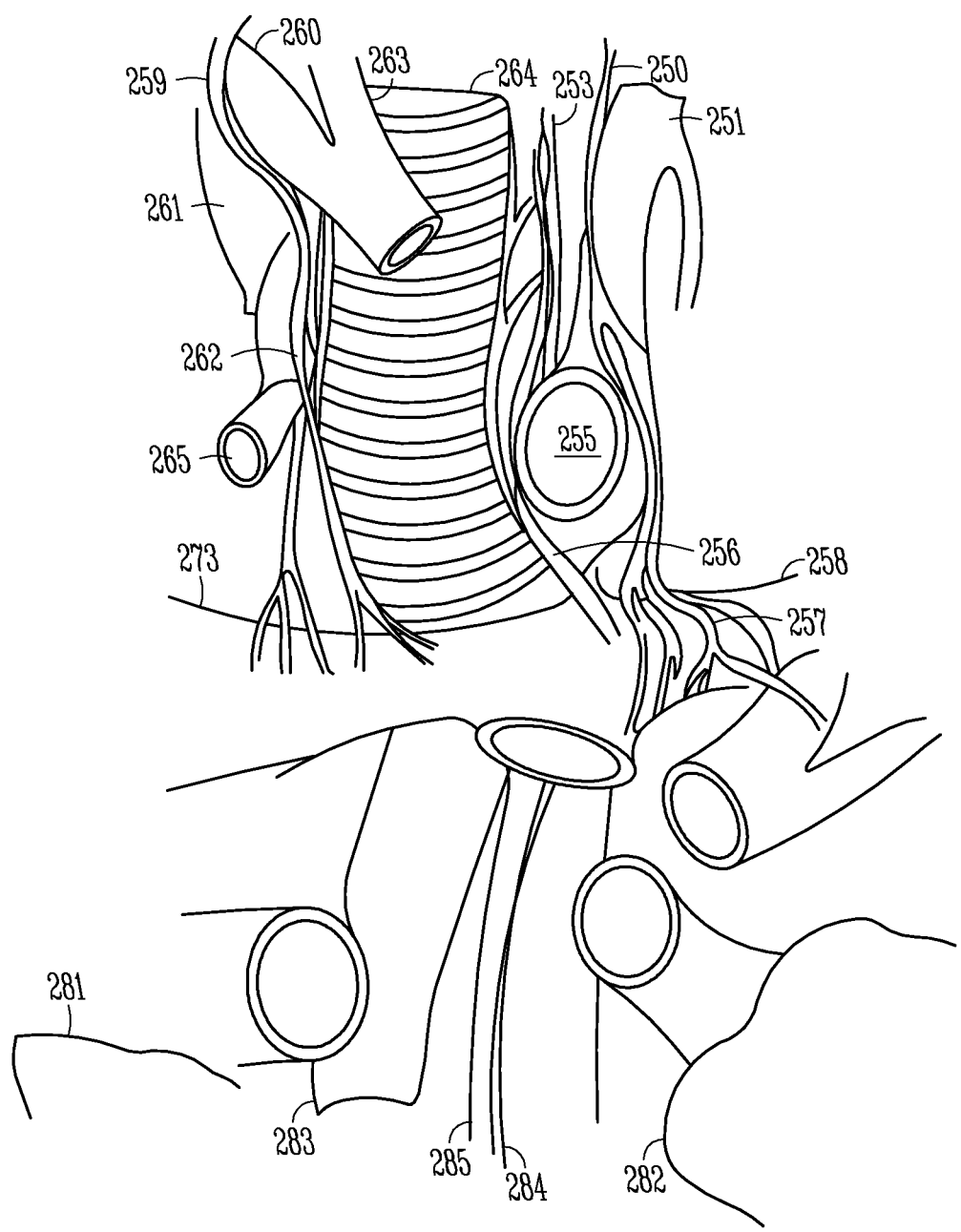
FIGS. 2A and 2B are illustrations of stimulation targets.
Figure 2B:
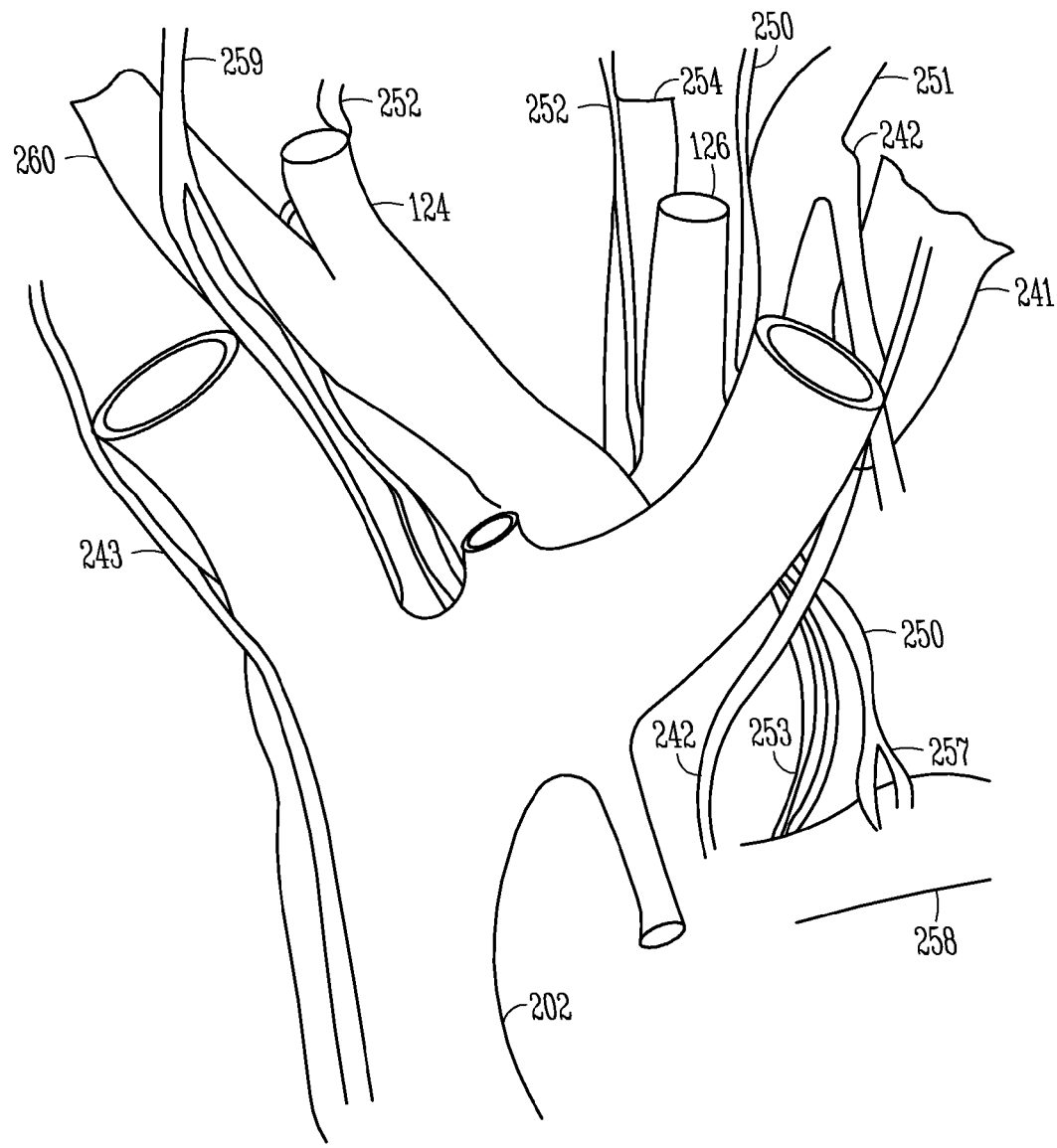
Figure 2C:
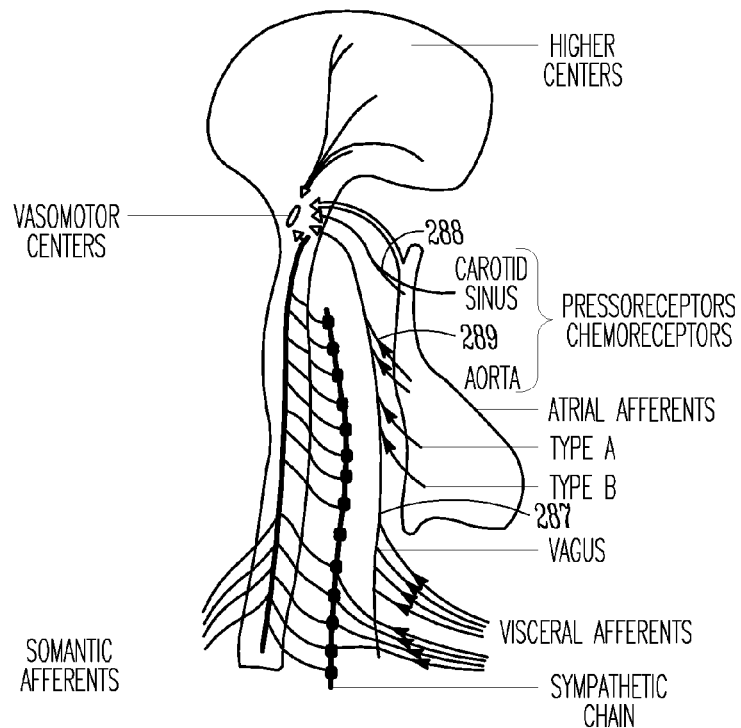
FIGS. 2C and 2D show neural pathways.
Figure 3A:
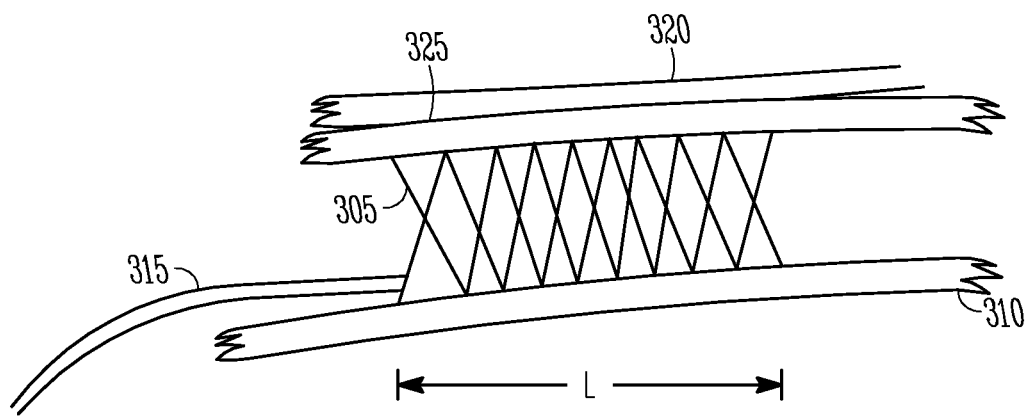
FIGS. 3A and 3B are illustrations of expandable electrodes chronically implanted in a blood vessel.
Figure 3B:
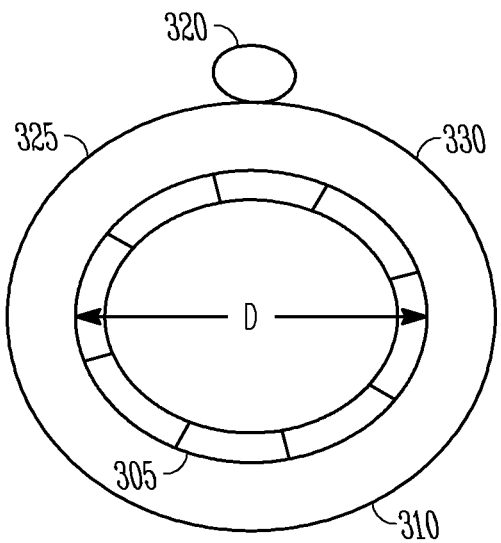
Figure 4:
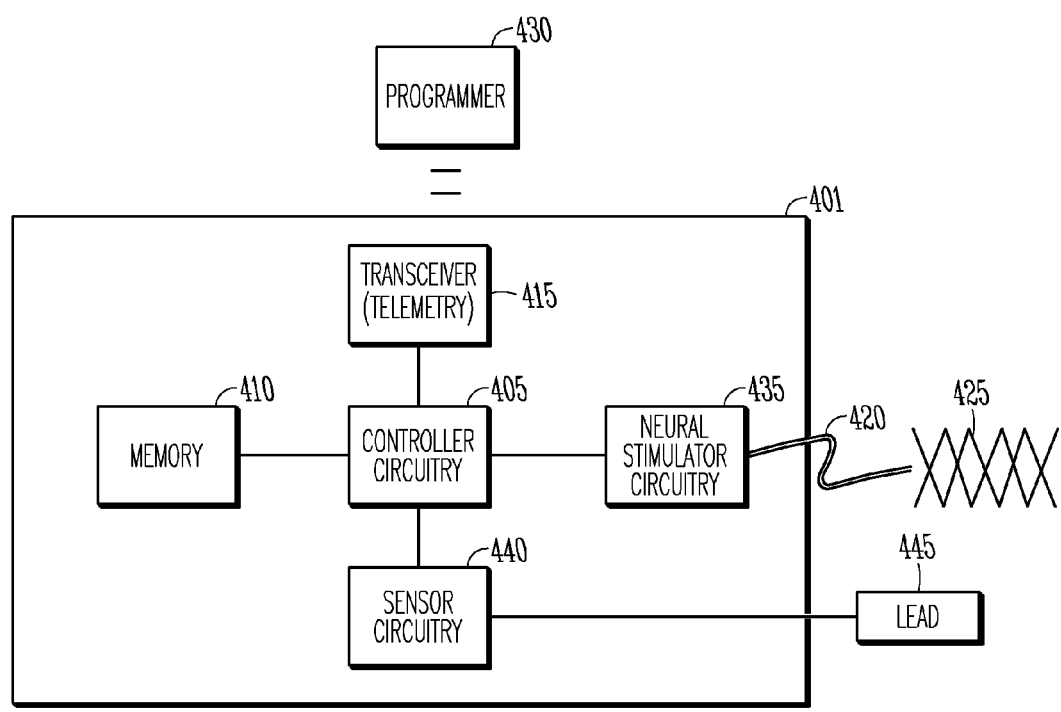
FIG. 4 is a schematic illustration of an implantable system for delivering transvascular stimulation.
Figure 5:
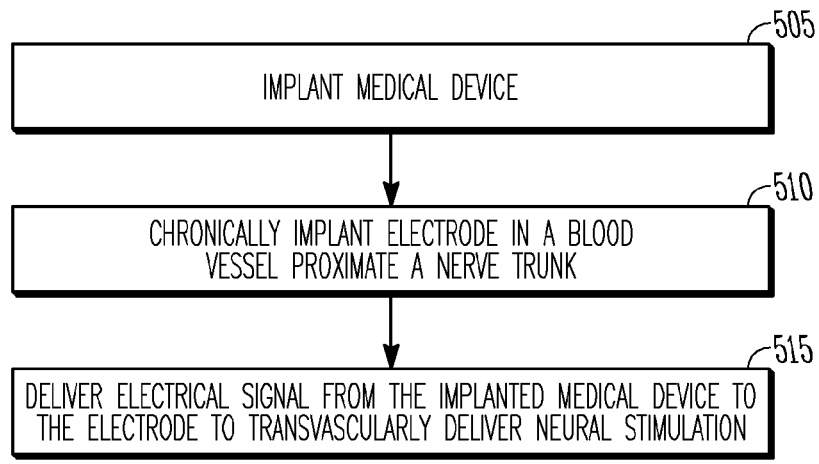
FIGS. 5 and 6 are flowcharts that illustrate methods of delivering transvascular stimulation.
Figure 6:
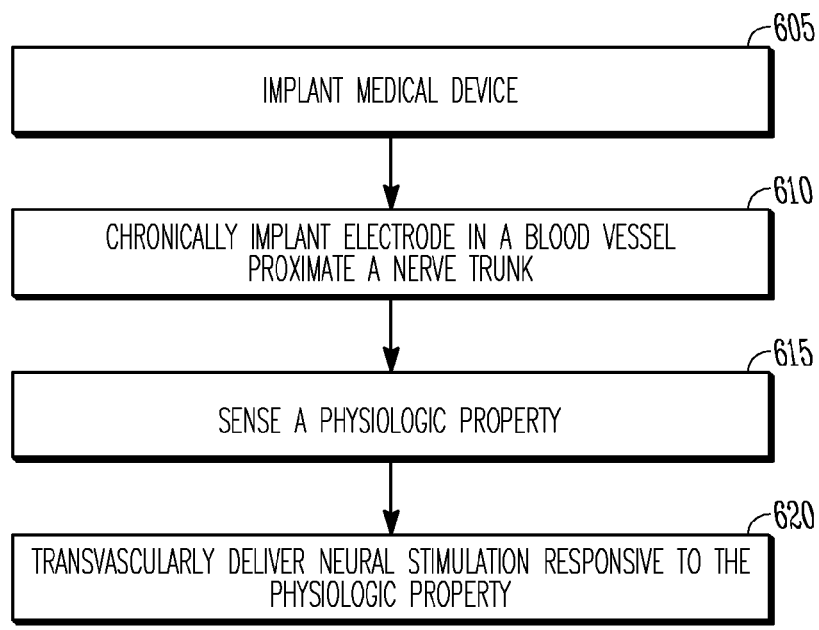

FIGS. 1B-1E and FIGS. 2A-2B illustrate examples of electrode placement. FIGS. 2B-2C show neural pathways. FIGS. 3A-3B show an example an electrode implanted in a blood vessel. FIG. 4 shows a schematic representation of an example of an implantable system for delivering transvascular stimulation. FIGS. 5 and 6 are flow charts that illustrate methods of delivering transvascular stimulation.

Electrode Examples

FIG. 3A is shows a cross-section of an example expandable electrode 305 implanted in a blood vessel 310. In an example, the expandable electrode includes a mesh, at least part of which is electrically conductive. In an example, the expandable electrode is formed from Platinum or Platinum-Iridium. In an embodiment, the expandable electrode 305 is similar to a stent.

Referring again to FIG. 3A, a nerve trunk 320 extends on or near an extravascular surface 325 of the blood vessel 310. An expandable electrode 305 is implanted at or near a location in the blood vessel where the nerve trunk 320 crosses the blood vessel. In an example, the expandable electrode transmits neural stimulation energy through a predetermined surface area of the wall of a blood vessel. In an example, this predetermined area is about 0.25 to 5 cm$^2$. In an example, the expandable electrode has a length L that provides enough surface area that there is at least some flexibility in the placement of the expandable electrode in the vessel with respect to the target nerve. In an example, the length of the expandable electrode is about 0.5 to 2.0 cm.

In an example, the entire surface area of the expandable electrode that touches the blood vessel wall is conductive. In an alternative example, at least a part of the surface area of the electrode is non-conductive. For example, an electrode can be formed and positioned to deliver stimulation to through a conductive part of the electrode to a portion 330 (FIG. 3B) of a blood vessel that is proximate a nerve.

FIG. 3B shows an end view of the blood vessel and electrode of FIG. 3A. The expandable electrode has an expanded diameter D (shown in FIG. 3B) that is sized for implantation in a blood vessel of a particular size range. In one example, where the electrode is size for implantation in the internal jugular vein, the expanded diameter D is about 0.5 to 1.5 cm, and the length L of the electrode is about 1.0 cm.

In an example, the expandable electrode is covered with a drug, such as a drug that prevents occlusion, or a drug that reduces inflammation of the blood vessel near the electrode.

The expandable electrode 305 is coupled to a power source that delivers an electrical stimulation. In FIG. 3A, the illustrated expandable electrode 305 is coupled to a lead 315. The lead 315 is coupled to an implantable system or device that includes control circuitry, such as the device shown in FIG. 1 or the system shown in FIG. 4.

Electrode Placement and Nerve Targets

The electrode may be implanted in various locations in the body, including a variety of locations near a trunk or branch of a sympathetic or parasympathetic nerve system.

Referring again to the example shown in FIG. 1A, the location of implanted electrodes 295, 296 is denoted by an X. The implanted electrodes 295, 296 each transvascularly stimulate a sympathetic nerve or a parasympathetic nerve. In an example, the electrode 295 transvascularly stimulates a peripheral nerve trunk. Examples of a peripheral nerve trunk include the vagus nerve 287, aortic nerve 288, and carotid sinus nerve 289, which are shown in FIG. 2C. In another example, the electrode 295 stimulates a nerve branch, such as a vagal cardiac branch.

FIGS. 1B, 1C, and 1D show examples of blood vessels in which the electrode can be implanted. FIG. 1B shows an implantable device 290, leads 291, 292, 293 extending into a heart 201 and a superior vena cava 202, an aortic arch 203, and a pulmonary artery 204. Leads extending into the heart are shown as dotted lines. For simplicity, electrodes are denoted with an X. Lead 291 and electrode 298 are inserted in the superior vena cava (SVC) 202. The electrode 298 is used to transvascularly stimulate a nerve or nerve trunk on or near the SVC 202. CRM lead 292 is intravascularly inserted through a peripheral vein into the coronary sinus and into the left ventricle. Electrode 299 is implanted in the coronary sinus and coupled to the CRM lead 292. FIG. 1B also shows electrodes 294 and 295, which are examples of sensing or pacing electrodes located in the right and left ventricles respectively. Physiological data sensed by one or both of the electrodes 294, 295 is processed by the device 290, and a responsive neurostimulation therapy is delivered by one or more of the electrodes 298, 299.

FIGS. 1C and 1D illustrate other bloods vessels on the right side and left side of the heart respectively in which an electrode is implantable. FIG. 1C shows the right atrium 267, right ventricle 268, sinoatrial node 269, superior vena cava 202, inferior vena cava 270, aorta 271, right pulmonary veins 272, and right pulmonary artery 273. FIG. 1D shows the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. An electrode can be implanted in one or more of the blood vessels listed above at a location where a nerve, nerve branch, or nerve trunk passes an extravascular surface of the blood vessel. The implanted electrode transvascularly stimulates a nerve, nerve branch, or nerve trunk through the blood vessel. In one example, an electrode is implanted in the SVC 202 near a nerve a vagal nerve trunk. In another example, an electrode is implanted in the coronary sinus 278 near a vagal nerve trunk.

In another example, a cardiac fat pad is transvascularly stimulated by an implanted electrode. FIG. 1C illustrates a cardiac fat pad 274 between the superior vena cava and aorta. FIG. 1D illustrates a cardiac fat pad 279 located proximate to the right cardiac veins and a cardiac fat pad 280 located proximate to the inferior vena cava and left atrium. An electrode implanted in the superior vena cava, aorta, cardiac veins, or inferior vena cava stimulates nerve endings in fat pad 274 or 279. Nerve endings in the fat pad 280 are stimulated by an electrode located in the coronary sinus.

Referring now to FIG. 1E, in an example, electrodes 131, 132, 133, 134 are implanted at locations in blood vessels near a vagus nerve. Portions of arteries are shown cut-away so that the electrodes are visible in the figure. The aortic arch 116, pulmonary artery 118, carotid arteries 124, 126 and subclavian arteries 128, 130 are shown in FIG. 1E. The right vagus nerve trunk 120 extends near carotid artery 124 and subclavian artery 128. The left vagus nerve 122 extends near carotid artery 126 and subclavian artery 130. Electrode 131 is implanted in carotid artery 124. The illustrated electrode 131 is an expandable electrode such as a stent. Electrode 132 is implanted in carotid artery 126. Electrode 133 is implanted in subclavian artery 128. Electrode 134 is implanted in subclavian artery 130. Electrode 140 is implanted in the carotid sinus 141 near the carotid sinus nerve 142. In an example, only one of electrodes 131, 132, 133, 134, 140 is implanted in a patient. In another example, two or more electrodes are implanted in a patient and used to transvascularly stimulate a nerve trunk.

FIGS. 2A and 2B provide additional illustrations of nerve target examples near the heart. FIG. 2A shows left vagus nerve 250 extending next to a subclavian artery 251. Various nerves extend around the arch of the aorta 255. Vagus nerve 250 also extends past the ligamentum arteriosum 256. The anterior pulmonary plexus 257 crosses the left pulmonary artery 258. Right vagus nerve 259 extends past a subclavian artery 260 and the cupola of pleura 261. Cardiac nerves 262 extend past the brachiocephalic trunk 263 near the trachea 264. Cardiac nerves 262 also extend past the arch of an azygos vein 265 to the right pulmonary artery 273. In the lower portion of FIG. 2A appear the right lung 281, left lung 282, esophagus 283, a lower portion 284 of the left vagus nerve 250, and a lower portion 285 of the aorta. FIG. 2B shows a left phrenic nerve 240 extending past a cupola of pleura 241, an internal thoracic artery 242, and left pulmonary artery 258 Vagus nerve 250, recurrent laryngeal nerves 252, cardiac nerves 253, and the anterior pulmonary plexus 257 extend near the left pulmonary artery 258 and ligamentum arteriosum. An expandable electrode, such as a stent, is chronically implantable in the blood vessels shown in FIG. 2A or 2B to transvascularly stimulate a nerve or nerve trunk that extends on or near the blood vessel. In one example, the vagus nerve is transvascularly stimulated from the azygos vein 265 or internal jugular vein.

Figure 2D:
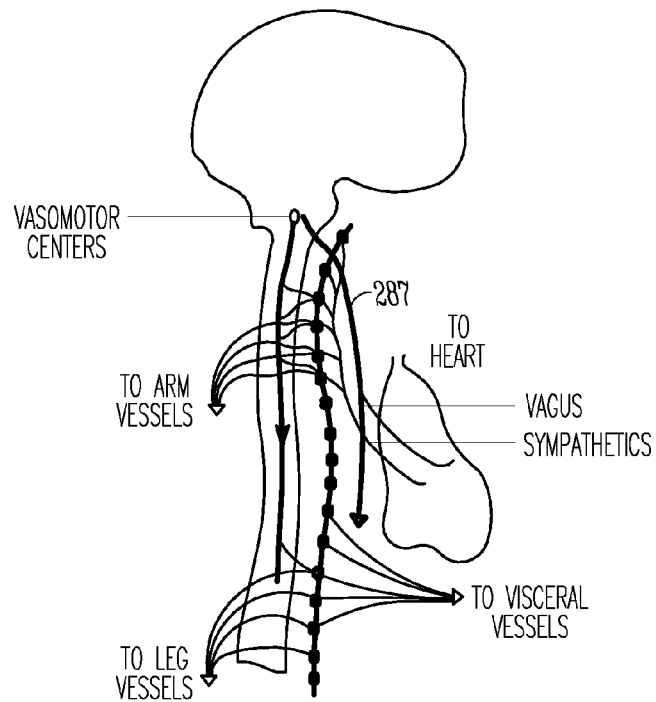

FIGS. 2C and 2D show nerve pathways. FIG. 2C generally illustrates afferent nerves to vasomotor centers. An afferent nerve conveys impulses toward a nerve center. A vasomotor center relates to nerves that dilate and constrict blood vessels to control the size of the blood vessels. FIG. 2D generally illustrates efferent nerves from vasomotor centers. An efferent nerve conveys impulses away from a nerve center. Afferent and efferent nerves can be stimulated transvascularly.

Figure 2E:
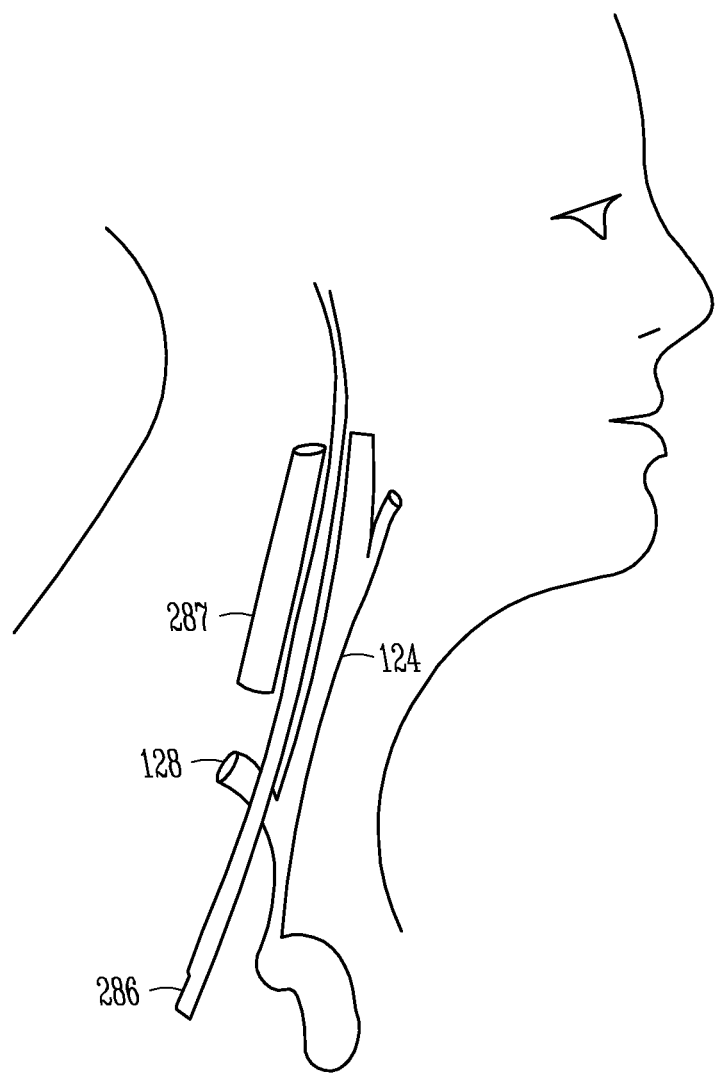
FIG. 2E is an illustration of an internal jugular vein near a vagus nerve.

FIG. 2E shows the vagus nerve 286 near the internal jugular vein 287. In an example, the vagus nerve 286 is transvascularly stimulated from the internal jugular vein 287. A common carotid artery 124 and subclavian artery 128 are also shown in FIG. 2E.

In other examples, nerve trunks innervating other organs, such as the lungs or kidneys are transvascularly stimulated. In an example, an expandable electrode such as a stent is implanted in a blood vessel proximate a nerve or nerve trunk that innervates the lungs or kidneys.

Device and System

Referring again to the example shown in FIG. 1A, an implantable device 100 is coupled to a lead 200 that is inserted into a blood vessel and coupled to an electrode 295. An electrical signal is delivered through the lead 200 to the electrode 295, which transvascularly stimulates a nerve on an extravascular surface of the blood vessel. The device 100 can optionally also deliver cardiac resynchronization therapy (CRT) through one or more CRT leads that are threaded intravenously into the heart. The CRT leads connect the device 100 to electrodes 300 that are used for sensing or pacing of the atria and/or ventricles. Transvascular stimulation electrode 296 is coupled to a CRT lead. Some embodiments process intrinsic electrical heart signals and deliver a responsive neural stimulation therapy through one of the electrodes 295, 296. An optional satellite unit 110 includes an electrode for neural stimulation and a communication circuit that communicates with the device 100 via a wireless link or conduction through the body. The satellite unit 110 electrode is implanted in a blood vessel, such as an internal jugular vein, to transvascularly stimulate a nerve, such as a vagus nerve, through the wall of the blood vessel.

FIG. 4 is a schematic illustration of an example transvascular stimulation system that includes an implantable device 401, an electrical lead 420 coupled to the implantable device 401, and an expandable stimulation electrode 425. The implantable device includes a controller circuit 405, a memory circuit 410, a telemetry circuit 415, and a neural stimulation circuit 435. The controller circuit 405 is operable on instructions stored in the memory circuit to deliver an electrical stimulation therapy. Therapy is delivered by the neural stimulation circuit 435 through the lead 420 and the electrode 425. The telemetry circuit 415 allows communication with an external programmer 430. The illustrated system also includes optional sensor circuitry 440 that is coupled to a lead 445. The controller circuit 405 processes sensor data from the sensor circuitry and delivers a therapy responsive to the sensor data.

Therapies

Neural stimulation therapies can be used to treat one or more of a variety of conditions, including but not limited to arrhythmias, heart failure, hypertension, syncope, or orthostatic intolerance. In an example, an efferent peripheral nerve is transvascularly stimulated by an implanted expandable electrode. In another example, an afferent peripheral nerve is stimulated.

In an example, electrical stimulation is transvascularly delivered to a parasympathetic nerve to reduce chronotropic, ionotropic, and dromotropic responses in the heart. In a therapy example, electrical stimulation is transvascularly delivered to a parasympathetic nerve trunk during heart failure. In another therapy example, electrical stimulation is transvascularly delivered to a parasympathetic nerve trunk following a myocardial infarction to protect against arrhythmias or prevent cardiac remodeling.

Transvascular stimulation of a vagus nerve trunk is used in a number of therapies. In an example, vagal nerve stimulation simultaneously increases parasympathetic tone and decreases sympathetic myocardial tone. In an example, a vagus nerve trunk is transvascularly stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, vagal stimulation from the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, transvascular neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by transvascularly stimulating a sympathetic nerve trunk. In another example, the ionotropic state of the heart is increased by transvascularly stimulating a sympathetic nerve trunk.

Methods for Delivering Transvascular Stimulation

Referring now to FIG. 5, an example method of delivering transvascular neural stimulation includes implanting a medical device, at 505. At 510, an electrode is chronically implanted in a blood vessel near a nerve trunk, such as a cardiac peripheral nerve trunk. In an example, the electrode is an expandable electrode, such as a stent. In an example, the expandable electrode has an expanded diameter that is dimensioned to fix the electrode in place by frictional forces. In an example, the expandable electrode includes a drug-eluting coating that prevents occlusion or prevents inflammation of vascular walls or nerves that receives electrical stimulation from the electrode. In an example, the electrode is implanted in a blood vessel at a location where the nerve trunk extends along an extravascular surface of the blood vessel. In an example, the electrode is implanted in a blood vessel near a peripheral nerve trunk. In an example, the peripheral nerve trunk includes a sympathetic or parasympathetic nerve. In an example, the electrode is implanted near a vagal cardiac nerve in a blood vessel such as the SVC, coronary sinus, or an azygos vein. In another example, the electrode is implanted in an internal jugular vein.

Returning to FIG. 5, at 515, an electrical signal is delivered from the implanted device to the electrode to transvascularly deliver neural stimulation to a nerve trunk near the blood vessel. In an example, the electrode delivers an electric pulse therapy that is sufficient to elicit depolarization of a target nerve. In an example, the stimulation therapy delivers about 1-10 milliamps of electrical stimulation. In an example, the controller delivers a pulse train of about 10-120 hertz to the electrode. In one example, a pulse train of about 20 hertz is used. In an example, delivery of transvascular neural stimulation near the heart is timed to occur during the cardiac refractory period to prevent fibrillation.

In an example, transvascularly stimulating a parasympathetic nerve inhibits cardiac remodeling or delivers an antiarrhythmia therapy following a myocardial infarction. In another example, transvascularly stimulating a sympathetic nerve delivers an antibradycardia therapy.

FIG. 6 is a flow chart that illustrates another method. A medical device is implanted at 605. At 610, an electrode is chronically implanted in a blood vessel near a nerve trunk. At 615, a physiologic property is sensed. In an example, an intrinsic electrical heart signal is detected. In another example, blood pressure is detected. At 620, neural stimulation responsive to the sensed physiologic property is transvascularly delivered through the implanted electrode.

What is claimed is:

1. An implantable apparatus for treating hypertension, comprising:
    an expandable electrode chronically implantable in a blood vessel and configured to abut an intravascular surface of the blood vessel;
    an implantable pulse generator configured to use the electrode in the blood vessel to transvascularly deliver electrical stimulation from the electrode through a wall of the blood vessel to a targeted nerve on or near an extravascular surface of the blood vessel; and
    a controller and a memory configured to store instructions operable on by the controller to deliver an electrical stimulation therapy to treat hypertension using electrical stimulation of the nerve from the electrode in the blood vessel.

2. The apparatus of claim 1, wherein the nerve is a vagus nerve or a branch of the vagus nerve, and the implantable pulse generator is configured to use the electrode in the blood vessel to transvascularly stimulate the vagus nerve or the branch of the vagus nerve.

3. The apparatus of claim 2, wherein the blood vessel is a pulmonary artery, and the implantable pulse generator is configured to use the electrode in the pulmonary artery to transvascularly stimulate the vagus nerve or the branch of the vagus nerve.

4. The apparatus of claim 2, wherein the blood vessel is an internal jugular vein, and the implantable pulse generator is configured to use the electrode in the internal jugular vein to transvascularly stimulate the vagus nerve.

5. The apparatus of claim 2, wherein the blood vessel is an aortic arch, and the implantable pulse generator is configured to use the electrode in the aortic arch to transvascularly stimulate the vagus nerve.

6. The apparatus of claim 2, wherein the blood vessel is an azygos vein, and the implantable pulse generator is configured to use the electrode in the azygos vein to transvascularly stimulate the vagus nerve.

7. The apparatus of claim 1, wherein the blood vessel is a subclavian artery and the nerve is a cardiac nerve, and the implantable pulse generator is configured to use the electrode in the subclavian artery to transvascularly stimulate the cardiac nerve.

8. The apparatus of claim 1, wherein the nerve is a parasympathetic nerve.

9. The apparatus of claim 1, the nerve is a carotid sinus nerve, and the implantable pulse generator is configured to use the electrode in the blood vessel to transvascularly stimulate the carotid sinus nerve.

10. The apparatus of claim 1, wherein the expandable includes a drug-eluting component.

11. The apparatus of claim 10, wherein the drug-eluting component is configured to elute a drug to reduce inflammation.

12. The apparatus of claim 10, wherein the drug-eluting component is configured to elute a drug to prevent occlusion.

13. The apparatus of claim 1, wherein the expandable electrode includes a stent.

14. The apparatus of claim 1, wherein the expandable electrode includes a mesh, and at least part of the mesh is conductive.

15. The apparatus of claim 1, wherein the blood vessel is an internal jugular vein and the nerve is the carotid sinus nerve, and the implantable pulse generator is configured to use the electrode in the internal jugular vein to transvascularly stimulate the cardiac sinus nerve.

16. The apparatus of claim 1, wherein the blood vessel is a carotid artery and the nerve is the carotid sinus nerve, and the implantable pulse generator is configured to use the electrode in the carotid artery to transvascularly stimulate the cardiac sinus nerve.

17. The apparatus of claim 1, wherein the blood vessel is a blood vessel proximate to a nerve that innervates a kidney, wherein the implantable pulse generator is configured to use the electrode in the blood vessel to transvascularly stimulate the nerve that innervates the kidney.

18. A method for treating hypertension, comprising:
    chronically implanting an expandable electrode in a blood vessel in a patient who is indicated for a hypertension therapy, including expanding the electrode to abut an intravascular surface of the blood vessel proximate to a targeted nerve on or near an extravascular surface of the blood vessel; and
    treating hypertension, including using an implantable pulse generator and the electrode in the blood vessel to transvascularly deliver electrical stimulation from the electrode through a wall of the blood vessel to the nerve on or near the extravascular surface of the blood vessel.

19. The method of claim 18, wherein the blood vessel is an internal jugular vein and the nerve is a carotid sinus nerve, wherein treating hypertension includes using the implantable pulse generator and the electrode chronically implanted in the internal jugular vein to stimulate the carotid sinus nerve.

20. The method of claim 18, wherein the blood vessel is a carotid artery and the nerve is a carotid sinus nerve, wherein treating hypertension includes using the implantable pulse generator and the electrode chronically implanted in the carotid artery to stimulate the carotid sinus nerve.

21. The method of claim 18, wherein the blood vessel is a pulmonary artery, and the nerve is a vagus nerve or a branch of the vagus nerve, wherein treating hypertension includes using the implantable pulse generator and the electrode chronically implanted in the pulmonary artery to stimulate the vagus nerve or the branch of the vagus nerve.

22. The method of claim 18, wherein the blood vessel is an internal jugular vein and the nerve is a vagus nerve, wherein treating hypertension includes using the implantable pulse generator and the electrode chronically implanted in the internal jugular vein to stimulate the vagus nerve.

23. The method of claim 18, wherein the blood vessel is an aortic arch and the nerve is a vagus nerve, wherein treating hypertension includes using the implantable pulse generator and the electrode chronically implanted in the aortic arch to stimulate the vagus nerve.

24. The method of claim 18, wherein the blood vessel is an azygos vein and the nerve is a vagus nerve, wherein treating hypertension includes using the implantable pulse generator and the electrode chronically implanted in the azygos vein to stimulate the vagus nerve.

25. The method of claim 18, wherein the blood vessel is a subclavian artery and the nerve is a vagus nerve, wherein treating hypertension includes using the implantable pulse generator and the electrode chronically implanted in the subclavian artery to stimulate the vagus nerve.

26. The method of claim 18, wherein chronically implanting an expandable electrode in a blood vessel includes chronically implanting an expandable electrode with a drug-eluting component configured to elute a drug to reduce inflammation.

27. The method of claim 18, wherein chronically implanting an expandable electrode in a blood vessel includes chronically implanting an expandable electrode with a drug-eluting component configured to elute a drug to prevent occlusion.

28. The method of claim 18, wherein chronically implanting an expandable electrode in a blood vessel includes chronically implanting the electrode in a blood vessel proximate to a nerve that innervates a kidney, and treating hypertension includes using the implantable pulse generator and the electrode to stimulate the nerve that innervates the kidney.

* * * * *